US00PP37106P2

(12) United States Plant Patent
Sakazaki

(10) Patent No.: US PP37,106 P2
(45) Date of Patent: Nov. 25, 2025

(54) ***HYDRANGEA* PLANT NAMED 'WNHYDFBLAMH'**

(50) Latin Name: ***Hydrangea* hybrid**
Varietal Denomination: WNHYDFBLAMH

(71) Applicant: Wingen LLC, Mustang Ridge, TX (US)

(72) Inventor: Ushio Sakazaki, Taga-cho (JP)

(73) Assignee: WinGen LLC, Mustang Ridge, TX (US)

( * ) Notice: Subject to any disclaimer, the term of this patent is extended or adjusted under 35 U.S.C. 154(b) by 0 days.

(21) Appl. No.: 19/179,527

(22) Filed: Apr. 15, 2025

(51) Int. Cl.
*A01H 5/00* (2018.01)
*A01H 6/48* (2018.01)

(52) U.S. Cl.
USPC ..... Plt./250

(58) Field of Classification Search
USPC ..... Plt./226, 250
See application file for complete search history.

(56) References Cited

U.S. PATENT DOCUMENTS

PP31,120 P3 * 11/2019 Sakazaki ..... A01H 6/48 Plt./250
PP35,988 P2 * 7/2024 Sakazaki ..... Plt./250

* cited by examiner

*Primary Examiner* — Karen M Redden

(57) ABSTRACT

A new and distinct cultivar of *Hydrangea* plant named 'WNHYDFBLAMH' is disclosed, characterized by mophead inflorescences, emerging from both terminal and lateral buds. Sepals emerge greenish-white then stay pink (basic soil conditions) or light blue (acidic soil conditions) for the duration of inflorescence. Plants flower early, and have mounded, cascading habits. The new variety is a *Hydrangea*, typically produced as an outdoor ornamental plant.

4 Drawing Sheets

Latin name of the genus and species: *Hydrangea* hybrid. Variety denomination: 'WNHYDFBLAMH'.

BACKGROUND OF THE INVENTION

The new cultivar is a product of a planned breeding program conducted by the inventor, at a commercial nursery in Higashiomi, Shiga, Japan. The objective of the breeding program was to produce new mophead *Hydrangea* varieties with cascading habits. The crossing resulting in the new variety was made in May of 2017.

The seed parent is the variety *Hydrangea macrophylla*, 'Deep Purple', unpatented. The pollen parent is an unnamed, unpatented specimen of the variety *Hydrangea luteovenosa*.

The new variety was found and selected by the inventor in June of 2019 at the same nursery in Higashiomi, Shiga, Japan.

Asexual reproduction of the new cultivar 'WNHYDFBLAMH' was first performed during October of 2019 in Higashiomi, Shiga, Japan, by terminal cuttings. Through subsequent propagation, multiple additional generations have been reproduced, having shown that the unique features of this cultivar are stable and reproduced true to type.

SUMMARY OF THE INVENTION

The cultivar 'WNHYDFBLAMH' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'WNHYDFBLAMH.' These characteristics in combination distinguish 'WNHYDFBLAMH' as a new and distinct *Hydrangea* cultivar:

1. Mophead inflorescences which emerge from both terminal and lateral buds.
2. Sepals emerge greenish-white then stay pink (basic soil) or light blue (acidic soil) for the duration of inflorescence.
3. Cascading/trailing type habit.
4. Leaf shape and size is more narrowly elliptic than Hydrangea macrophylla but larger than *Hydrangea luteovenosa*.

PARENT COMPARISONS

Plants of 'WNHYDFBLAMH' are similar to plants of the seed parent in most horticultural characteristics, however, plants of 'WNHYDFBLAMH' differ in the following:

1. Leaves of the new variety are medium-sized, while leaves of the seed parent are large.
2. Flowers of the new variety set on terminal and lateral buds, while flowers of the seed parent set on only terminal buds.
3. Plants of the new variety flower earlier than plants of the seed parent.
4. Plants of the new variety have a weeping, cascading habit, while plants of the seed parent have an upright habit.

Plants of 'WNHYDFBLAMH' are similar to plants of the pollen parent in most horticultural characteristics, however, plants of 'WNHYDFBLAMH' differ in the following:

1. Leaves of the new variety are medium-sized, while leaves of the pollen parent are small.

2. Sepals of the new variety are larger than sepals of the pollen parent.
3. Inflorescences of the new variety are mophead, while inflorescences of the pollen parent are lacecap.

COMMERCIAL COMPARISONS

Plants of the new cultivar *Hydrangea* 'WNHYDFBLAMH' can be compared to the commercial variety *Hydrangea* 'USHYD0405', U.S. Plant Pat. No. 31,120. Plants of 'WNHYDFBLAMH' are similar to plants of 'USHYD0405' in most horticultural characteristics, however, plants of 'WNHYDFBLAMH' differ in the following:

1. Inflorescences of the new variety are mophead, while inflorescences of this comparator are lacecap.
2. Flowers of the new variety open greenish-white then stay pink and light blue for duration of inflorescence. Flowers of this comparator open and remain white.

Plants of the new cultivar *Hydrangea* 'WNHYDFBLAMH' can be compared to the commercial variety *Hydrangea* 'WNHYDFBVYWMH', U.S. Plant Pat. No. 35,989. Plants of 'WNHYDFBLAMH' are similar to plants of 'WNHYDFBVYWMH' in most horticultural characteristics, however, plants of 'WNHYDFBLAMH' differ in the following:

1. Flowers of the new variety open greenish-white then stay pink and light blue for duration of inflorescence. Flowers of this comparator open and remain white.

BRIEF DESCRIPTION OF THE PHOTOGRAPHS

The accompanying photograph in FIG. 1 illustrates in full color a typical plant of 'WNHYDFBLAMH' grown in a poly-greenhouse in Grand Haven, Michigan. This plant is approximately 2-3 years old, grown in a 2-gallon container and has been grown in acidic soil.

DETAILED BOTANICAL DESCRIPTION

Figure 1:
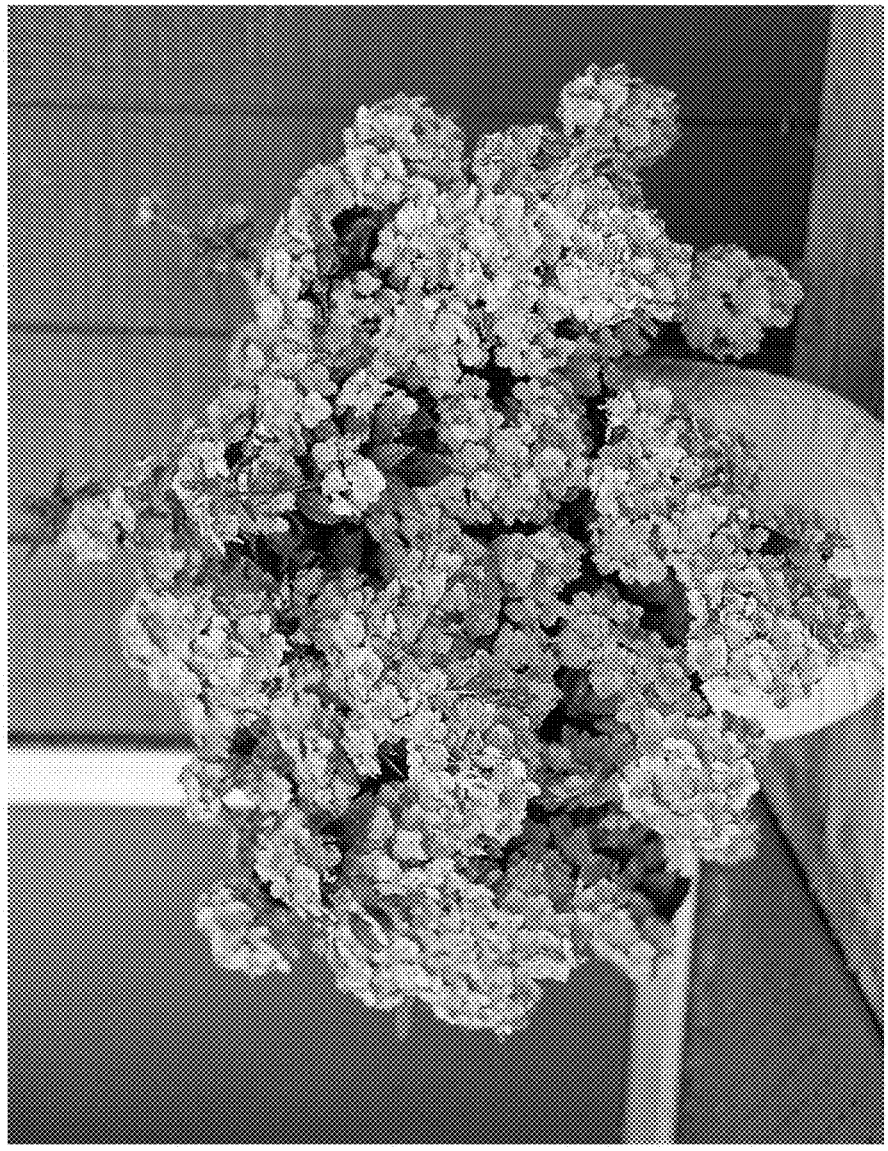
Figure 2:
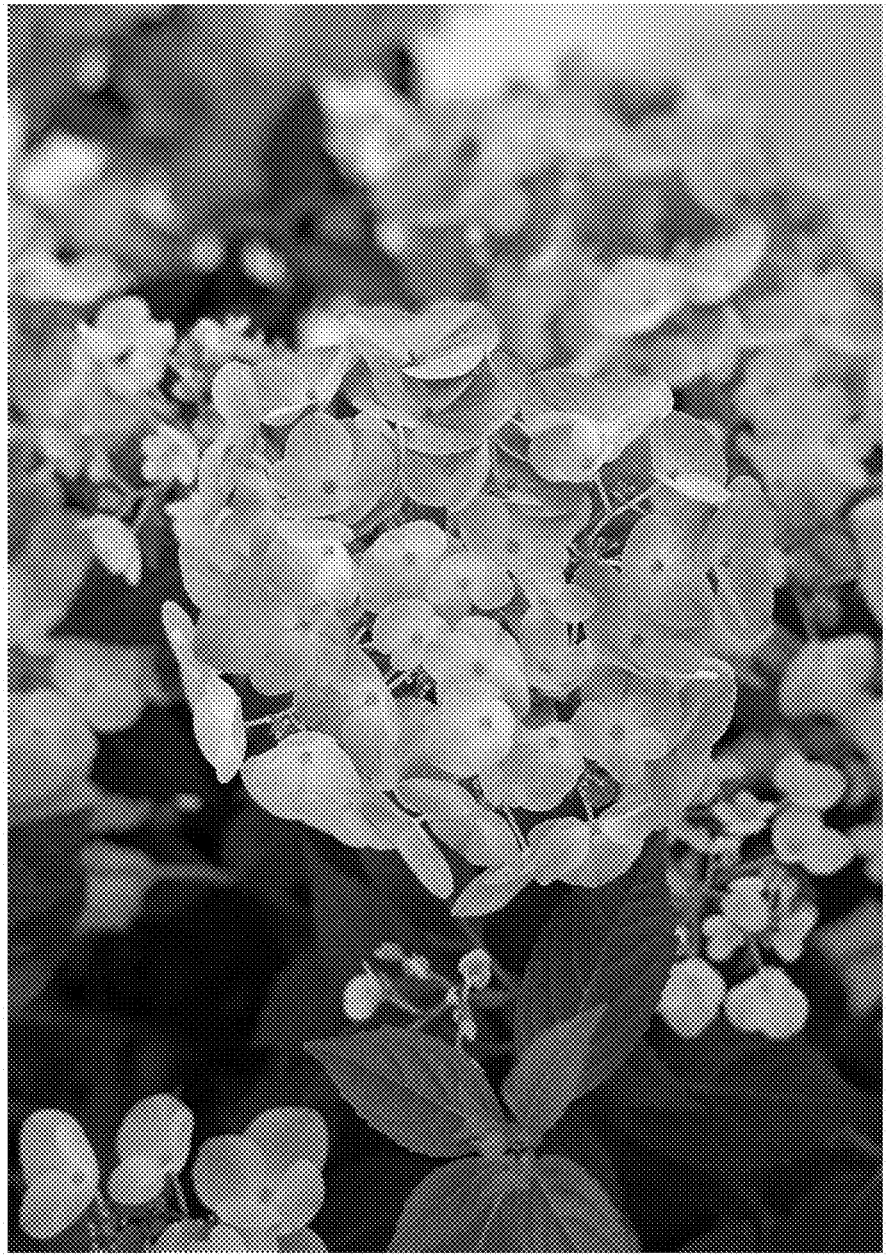
FIG. 2 illustrates in full color a close up of a mature inflorescence of 'WNHYDFBLAMH' given acidic treatment.
Figure 3:
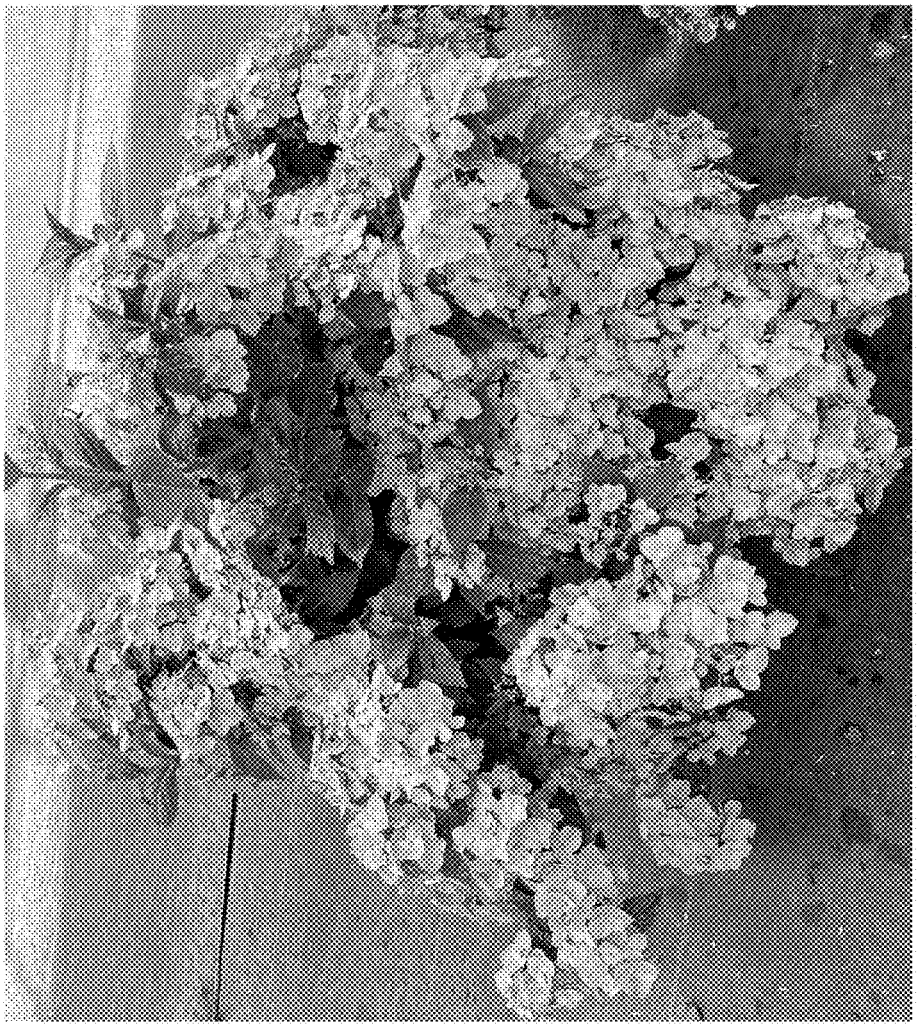
FIG. 3 illustrates in full color a typical plant of 'WNHYDFBLAMH' grown in a poly-greenhouse in Grand Haven that has been grown in basic soil conditions.
Figure 4:
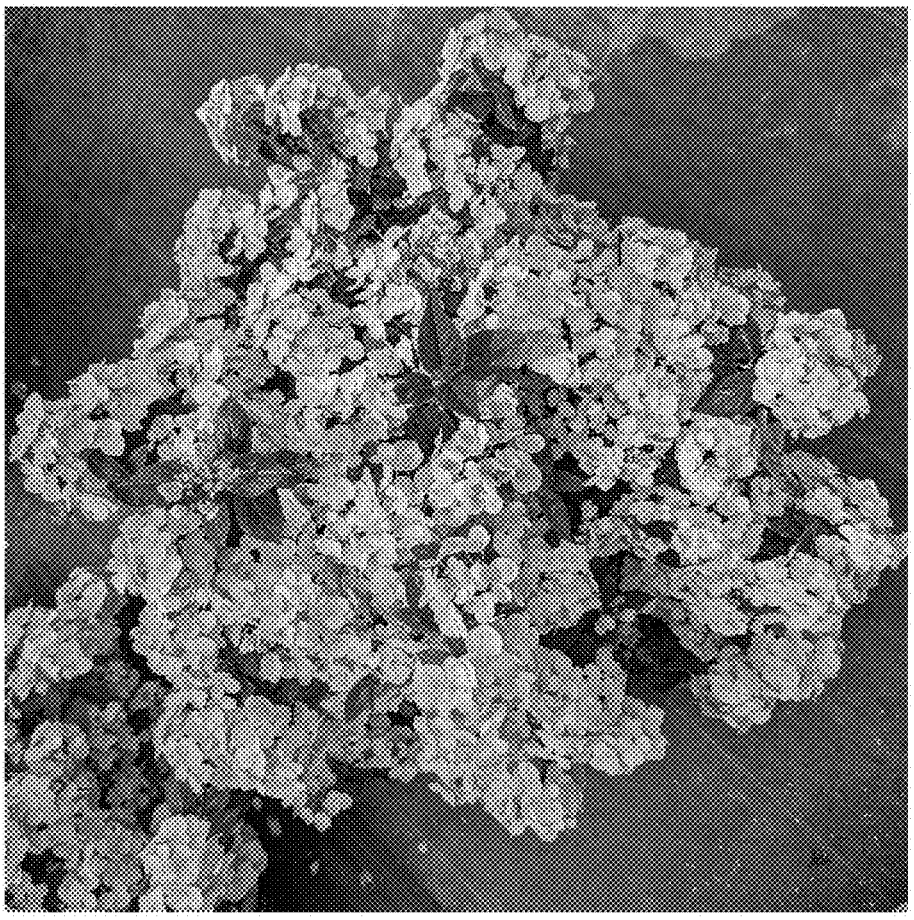
FIG. 4 illustrates in full color a typical plant in basic soil conditions of 'WNHYDFBLAMH' with mature inflorescences, more mature than that of FIG. 3. The photographs were taken using conventional techniques and although colors may appear different from actual colors due to light reflectance it is as accurate as possible by conventional photographic techniques.

In the following description, color references are made to the Royal Horticultural Society Colour Chart 2015, except where general terms of ordinary dictionary significance are used. The following observations and measurements describe 'WNHYDFBLAMH' plants grown outdoors in Grand Haven, Michigan. The plants were about 2 to 3 years old. Temperatures ranged from 5° C. to 10° C. at night to 18° C. to 27° C. during the day. No artificial light, photoperiodic treatments were given to the plants. Measurements and numerical values represent averages of typical plant types.

Botanical classification: *Hydrangea* hybrid 'WNHYDFBLAMH'.

PROPAGATION

Typical Method: Terminal cuttings.
Root Initiation: 5 to 7 days in the summer.
Time to Produce Rooted Cutting: 28 days in the summer.
Roots: Thin to medium, freely branching, fibrous, moderately dense. Beige to tan in color, not accurately measured with RHS chart.

PLANT

Growth Habit: Upwards and outwards in a drooping manner.
Shape: Mounded and cascading.
Height: 45 cm.
Plant Spread: 95 cm.
Pot Size of Plant Described: #3 container.
Age of Plant Described: Approximately 2 to 3 years.
Growth Rate: Moderate to fast.
Plant Vigor: High vigor.
Stem:
- *Branching*.—Basal.
- *Number of Lateral Branches*.—About 30.
- *Shape*.—Rounded, smooth.
- *Color*.—Immature: RHS Yellow-Green 146A. Mature: RHS Brown 200A.
- *Length*.—45 cm.
- *Width*.—5 mm.
- *Aspect*.—0 to 60°.
- *Strength*.—Good, somewhat flexible.
- *Pubescence*.—None.
- *Internode Length*.—6.5 cm.

FOLIAGE

Leaf:
- *Arrangement*.—Opposite.
- *Shape*.—Narrowly elliptic.
- *Length*.—9.2 cm.
- *Width*.—4 cm.
- *Apex*.—Acuminate.
- *Base*.—Cuneate.
- *Margin*.—Serrulate.
- *Texture of top surface*.—Glabrous, slightly glossy and coriaceous.
- *Texture of bottom surface*.—Glabrous, slightly glossy and coriaceous with pronounced venation.
- *Pubescence*.—None.
- *Color*.—Young Foliage Upper Side: RHS Yellow-Green 147A. Young Foliage Under Side: Near RHS Yellow-Green 147B. Mature Foliage Upper Side: RHS Green NN137A. Mature Foliage, Under Side: RHS Yellow-Green 147B.

Venation:
- *Type*.—Pinnate.
- *Color*.—Mature, Upper Side: RHS Yellow-Green 146A. Mature, Under Side: RHS Yellow-Green 146A.

Petiole:
- *Length*.—1 cm.
- *Width*.—2 mm.
- *Color*.—Upper Side: RHS Yellow-Green 146A, with Grey-Brown N199A tint. Under Side: RHS Yellow-Green 146A, with Grey-Brown N199A tint.

*Texture*.—Upper Side: Glabrous. Under Side: Glabrous.

INFLORESCENCE

Natural flowering season: June to July.
Inflorescence Type: Mophead.
Longevity of Entire Inflorescence: 3 weeks.
Panicle:
*Shape*.—Globular, with a flat base; compound umbel.
*Height*.—6 cm.
*Diameter*.—11 cm.
Fragrance: None.
Sterile Flowers:
*Flowers Per Inflorescence*.—50 to 75.
*Aspect*.—Upright and outward.
*Shape*.—Single whorl.
*Length*.—5 cm.
*Diameter*.—5 cm.
*Depth*.—1 mm.
*Persistence*.—Persistent.
*Longevity on Plant*.—3 weeks.
Bud:
*Length*.—3 mm.
*Diameter*.—2 mm.
*Shape*.—Obovate.
*Color*.—RHS Yellow-Green 144D.
Petals:
*Number per Flower*.—4.
*Arrangement*.—Cruciform.
*Shape*.—Elliptic.
*Tip*.—Acute.
*Base*.—Flattened.
*Margin*.—Entire.
*Length*.—2 mm.
*Width*.—1 mm.
*Texture*.—Upper side: Glabrous. Under side: Glabrous.
*Color*.—When Opening, Upper Side: Acidic: RHS Violet-Blue 98B. Basic: RHS Red-Purple 65B. When Opening, Under Side: Acidic: RHS Violet-Blue 98B. Basic: RHS Red-Purple 65C. Fully Opened, Upper Side: Acidic: RHS Violet-Blue 98B. Basic: RHS Red-Purple 65B. Fully Opened, Under Side: Acidic: RHS Violet-Blue 98B. Basic: RHS Red-Purple 65C.
Sepal:
*Number*.—4 to 5.
*Arrangement*.—Cruciform/stellate.
*Shape*.—Broadly ovate to orbicular.
*Tip*.—Broadly acute to obtuse.
*Base*.—Obtuse.
*Margin*.—Entire.
*Length*.—1.5 to 2 cm.
*Width*.—1.5 to 2 cm.
*Texture*.—Upper side: Soft and silky. Under side: Soft and silky.
*Color*.—When Opening, Upper Side: Acidic: RHS Yellow-Green 145B with Violet-Blue 98B marginally. Basic: RHS Yellow-Green 145B with Greyed-Red 181D marginally. When Opening, Under Side: Acidic: RHS Blue 101D. Basic: RHS Red-Purple 65C. Fully Opened, Upper Side: Acidic: RHS Violet-Blue 98C-D. Basic: RHS Red-Purple 65B. Fully Opened, Under Side: Acidic: RHS Blue 101D. Basic: RHS Red-Purple 65C.
Pedicel:
*Length*.—2 cm.
*Diameter*.—1 mm.
*Angle*.—45° relative to peduncle.
*Strength*.—Good, somewhat flexible.
*Texture*.—Very slightly pubescent.
*Color*.—Acidic: RHS Red-Purple 65B-C. Basic: RHS Red-Purple 65B-C.
Fertile Flowers:
*Flowers Per Inflorescence*.—About 5 to 10.
*Aspect*.—Upright.
*Shape*.—Round, single whorl of petals.
*Length*.—6 mm.
*Diameter*.—6 mm.
*Depth*.—4 mm.
*Persistence*.—Self-cleaning.
*Longevity on Plant*.—1 to 2 weeks.
Bud:
*Length*.—4 mm.
*Bud Diameter*.—3 mm.
*Bud Shape*.—Obovate.
*Bud Color*.—RHS Yellow-Green 144D.
Petals:
*Number per Flower*.—5.
*Arrangement*.—Stellate.
*Shape*.—Elliptic.
*Tip*.—Acute.
*Base*.—Flattened.
*Margin*.—Entire.
*Length*.—2 mm.
*Width*.—1.5 mm.
*Texture*.—Upper Side: Glabrous. Under Side: Glabrous.
*Color*.—When Opening, Upper Side: Acidic: RHS Violet-Blue 98B. Basic: RHS Red-Purple 65B. When Opening, Under Side: Acidic: RHS Violet-Blue 98B. Basic: RHS Red-Purple 65C. Fully Opened, Upper Side: Acidic: RHS Violet-Blue 98B. Basic: RHS Red-Purple 65B. Fully Opened, Under Side: Acidic: RHS Violet-Blue 98B. Basic: RHS Red-Purple 65C.
Sepal:
*Number*.—5.
*Arrangement*.—Stellate.
*Shape*.—Elliptic.
*Tip*.—Acute.
*Base*.—Fused.
*Margin*.—Entire.
*Length*.—1 mm.
*Width*.—1 mm.
*Texture*.—Upper Side: Glabrous. Under Side: Glabrous.
*Color*.—When Opening, Upper Side: Acidic: RHS Violet-Blue 98C. Basic: RHS Red-Purple N66D. When Opening, Under Side: Acidic: RHS Violet-Blue 98C. Basic: RHS Red-Purple N66D. Fully Opened, Upper Side: Acidic: RHS.Violet-Blue 98C Basic: RHS Red-Purple N66D. Fully Opened, Under Side: Acidic: RHS Violet-Blue 98C. Basic: RHS Red-Purple N66D.
Pedicel:
*Length*.—4 mm.
*Diameter*.—1 mm.
*Angle*.—45° relative to peduncle.
*Strength*.—Good, somewhat flexible.

*Texture*.—Very slightly pubescent.
*Color*.—Acidic: RHS Red-Purple 65B-C. Basic: RHS Red-Purple 65B-C.

REPRODUCTIVE ORGANS

Sterile Flower:
Stamens:
*Number*.—4 to 8.
*Filament Length*.—2 mm.
*Filament Color*.—Acidic: RHS Blue-Green 112B. Basic: RHS Red-Purple 63B.
Anther:
*Shape*.—Orbicular.
*Length*.—1 mm.
*Color*.—Acidic: RHS Yellow-Orange 18C with tints of Blue-Green 115B. Basic: RHS Yellow 8C. Pollen Amount: Sparse.
Pistil:
*Number*.—1.
*Length*.—3 mm.
Stigma:
*Shape*.—3-lobed, fused.
*Color*.—Acidic: RHS Blue-Green 112B. Basic: RHS Red-Purple 65D.
*Style Length*.—2.5 mm.
*Style Color*.—Acidic: RHS Violet-Blue 98C. Basic: RHS Red-Purple 63B.
Fertile Flower:
Stamens:
*Number*.—4 to 8.
*Filament Length*.—2 mm.
*Filament Color*.—Acidic: RHS Blue-Green 112B. Basic: RHS Red-Purple 63B.
Anther:
*Shape*.—Orbicular.
*Length*.—1 mm.
*Color*.—Acidic: RHS Yellow-Orange 18C with tints of Blue-Green 115B. Basic: RHS Yellow 8C.
*Pollen Amount*.—Sparse.
Pistil:
*Number*.—1.
*Length*.—3 mm.
Stigma:
*Shape*.—3-lobed, fused.
*Color*.—Acidic: RHS Blue-Green 112D. Basic: RHS Red-Purple 65D.
*Style Length*.—2.5 mm.
*Style Color*.—Acidic: RHS Violet-Blue 98C. Basic: RHS Red-Purple 63B.

OTHER CHARACTERISTICS

Fruit/Seed Production: Not observed.
Disease Resistance: Neither resistance nor susceptibility to the normal diseases and pests of *Hydrangea* has been observed.
Drought Tolerance and Cold Tolerance: The new cultivar can tolerate cold temperatures to approximately -31° C. and tolerates an upper temperature range to at least 38° C.
What is claimed is:
1. A new and distinct cultivar of *Hydrangea* plant named 'WNHYDFBLAMH' as illustrated and described herein.

* * * * *